United States Patent [19]

Grossi et al.

[11] Patent Number: 5,312,952

[45] Date of Patent: May 17, 1994

[54] POLYMERIZATION INHIBITOR FOR VINYL AROMATICS

[75] Inventors: Anthony V. Grossi, Torrington; Paul E. Stott, Sandy Hook; John M. DeMassa, South Norwalk; Howard S. Friedman, North Haven; Gerald J. Abruscato, Southington, all of Conn.

[73] Assignee: Uniroyal Chemical Company, Inc., Middlebury, Conn.

[21] Appl. No.: 872,563

[22] Filed: Apr. 23, 1992

[51] Int. Cl.$^5$ .................. C07C 309/28; C07C 317/14
[52] U.S. Cl. ........................ 558/46; 558/56; 558/58; 568/30; 568/33; 568/931
[58] Field of Search .................. 252/405, 406; 526/83, 526/84; 558/56, 58, 46; 568/33, 30, 706, 780, 931

[56] References Cited

U.S. PATENT DOCUMENTS

| | | | |
|---|---|---|---|
| 765,597 | 7/1904 | Sapper et al. | 558/58 |
| 2,020,727 | 7/1940 | Galloway | 568/706 |
| 2,289,804 | 7/1942 | Peterson et al. | 558/58 |
| 2,526,567 | 10/1950 | Drake et al. | 260/650 |
| 2,610,164 | 9/1952 | Gluesenkamp et al. | 558/56 |
| 3,364,172 | 1/1968 | Tocker | 524/260 |
| 3,745,188 | 7/1973 | Bottorff et al. | 558/58 |
| 3,812,194 | 5/1974 | Starer et al. | 558/56 |
| 3,818,102 | 6/1974 | Partos | 558/56 |
| 4,049,467 | 9/1977 | Rubin | 252/132 |
| 4,105,506 | 8/1978 | Watson | 203/9 |
| 4,116,934 | 9/1978 | Petersen et al. | 524/164 |
| 4,144,213 | 3/1979 | Patton | 252/406 |
| 4,178,330 | 12/1979 | Albright | 524/163 |
| 4,208,486 | 6/1980 | Patton | 252/406 |
| 4,246,188 | 1/1981 | Peterson et al. | 558/46 |
| 4,310,471 | 1/1982 | Oswald et al. | 558/56 |
| 4,459,152 | 7/1984 | Frankhauser et al. | 568/30 |
| 4,466,905 | 8/1984 | Butler et al. | 252/403 |
| 4,774,374 | 9/1988 | Abruscato et al. | 585/24 |
| 5,157,175 | 10/1992 | Lewis et al. | 585/5 |

FOREIGN PATENT DOCUMENTS 0234671 2/1987 European Pat. Off. .
655612 3/1965 France .

OTHER PUBLICATIONS

Pesticide Science, vol. 3, No. 5, 1972, London, GB, pp. 551–559, D. Brown, et al.: 'Factors affecting the activities of nitrophenol fungicides. III. Influence of substituents on the hydrogen bonding characteristics of nitro- and halogeno-phenols'.

Journal of the Chemical Society, 1955, Letchworth, GB, pp. 4391–4393, D. Woodcock 'Fungicidal activity and chemical constitution. Part IV. Synthesis of 5-n-alkyl-8-hydroxyquinolines', see p. 4392, 1st table.

Chemical Abstracts, vol. 74, No. 12, 22 Mar. 1971, Columbus, Ohio, U.S.; abstract No. 57818e, L. M. Gindin, et al.: "Extraction of nonferrous metals by phenols", p. 277.

Primary Examiner—Robert L. Stoll
Assistant Examiner—Valerie D. Fee
Attorney, Agent, or Firm—Jerome D. Drabiak

[57] ABSTRACT

This invention relates to a vinyl aromatic. Compounds of Structure (I):

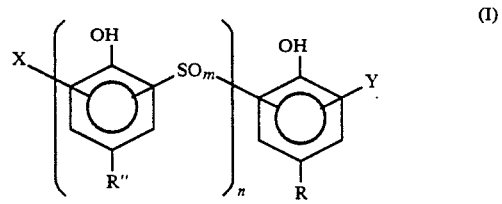

wherein R is $C_9$–$C_{20}$ alkyl, Y is $NO_2$, $SO_3R'$ or H, R' is $C_1$–$C_{20}$ alkyl, X is $NO_2$ or $C_1$–$C_{20}$ alkyl, and R" is H or $C_1$–$C_{20}$ alkyl, m is 2 or 3 and n is 0,1,2,3, with the proviso that when R is $C_9$ and n=0, X and Y may not both be $NO_2$.

5 Claims, No Drawings

POLYMERIZATION INHIBITOR FOR VINYL AROMATICS

FIELD OF THE INVENTION

This invention is directed to a polymerization inhibitor system for vinyl aromatic compounds. In particular, the polymerization inhibitor contains the active ingredient which is a reaction product of a $C_9$–$C_{20}$ alkyl phenol with sulfuric acid and nitric acid, believed to be structurally represented by a blend of compounds of structure (I)

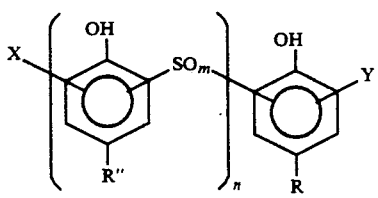

wherein R is $C_9$–$C_{20}$ alkyl, Y is $NO_2$, $SO_3R'$ or H, R' is $C_1$–$C_{20}$ alkyl, X is $NO_2$ or $C_1$–$C_{20}$ alkyl, and R" is H or $C_1$–$C_{20}$ alkyl, m is 2 or 3 and n is 0,1,2,3, with the proviso that when R is $C_9$ and n=0, then X and Y may not both be $NO_2$.

In other aspects, this invention is directed to a vinyl aromatic composition stabilized against polymerization by such polymerization inhibitor system, as well as to a method of stabilizing a vinyl aromatic composition against polymerization which method comprises adding an effective amount of such polymerization inhibitor system.

BACKGROUND OF THE INVENTION

Commercial processes for the manufacture of vinyl aromatic compounds such as monomeric styrene, divinyl benzene and lower alkylated styrenes (such as alpha-methylstyrene and vinyltoluene) typically produce products contaminated with various impurities, such as benzene, toluene and the like. These impurities must be removed in order for the monomer product to be suitable for most applications. Such purification of vinyl aromatic compounds is generally accomplished by distillation.

However, it is well known that vinyl aromatic compounds polymerize readily and that the rate of polymerization increases rapidly as the temperature increases. In order to prevent polymerization of the vinyl aromatic monomer under distillation conditions various polymerization inhibitors have been employed.

In general, the compounds which are commercially employed as such polymerization inhibitors are of the dinitrophenolic class. Thus, for example, Drake et al, in U.S. Pat. No. 2,526,567, show the stabilization of nuclear chlorostyrenes employing 2,6-dinitrophenols. Similarly, U.S. Pat. No. 4,105,506, to Watson, discloses the use of 2,6-dinitro-p-cresol as a polymerization inhibitor for vinyl aromatic compounds.

In addition, it has been disclosed by Butler et al, in U.S. Pat. No. 4,466,905, that, in the presence of oxygen, phenylenediamines in the distillation column together with 2,6-dinitro-p-cresol will reduce the amount of polymerization which occurs.

While dinitrophenols are effective polymerization inhibitors, there are several disadvantages associated with their use, either alone or in blends. For example, many dinitrophenols are solids that, if subjected to temperatures above their melting points, are unstable and may explode (see U.S. Pat. No. 4,457,806). Moreover, many dinitrophenols are highly toxic which requires special precautions in its use.

While such prior art inhibitors may inhibit the polymerization of vinyl aromatic compounds to some degree, it would be desirable to possess polymerization inhibitors which would more effectively delay the onset of polymerization and/or which would avoid the problem of high toxicity.

Accordingly, it is an object of this invention to provide an improved polymerization inhibitor system for the prevention of polymerization of vinyl aromatic compounds.

It is an additional object of this invention to provide an inhibitor system for the prevention of polymerization of vinyl aromatic compounds, which inhibitor system does not comprise toxic dinitrophenolic compounds.

Another object of this invention is to provide a vinyl aromatic polymerization inhibitor system which does not require air to function.

It is a further object of this invention to provide a vinyl aromatic composition which is stabilized against polymerization.

It is yet another object of this invention to provide an improved method for inhibiting the polymerization of vinyl aromatic compounds.

The foregoing and additional objects will become more fully apparent from the following description and accompanying Examples.

DETAILED DESCRIPTION OF THE INVENTION

The active compounds for polymerization inhibition systems of this invention are believed to be generally represented by structure (I)

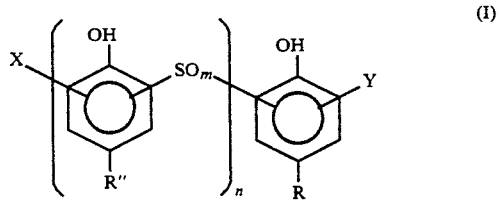

wherein R is $C_9$–$C_{20}$ alkyl, Y is $NO_2$, $SO_3R'$ or H, R' is $C_1$–$C_{20}$ alkyl, X is $NO_2$ or $C_1$–$C_{20}$ alkyl, and R" is H or $C_1$–$C_{20}$ alkyl, m is 2 or 3 and n is 0, 1, 2, 3, with the proviso that when R is $C_9$ and n=0, X and Y may not both be $NO_2$.

The more preferred are those represented by structure (III), where n=0, X and Y are ortho to the OH and X=$NO_2$, Y is as defined for (I) and R is $C_{10}$–$C_{20}$ alkyl.

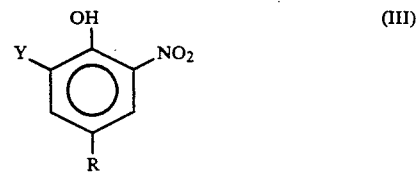

These compounds generally exist as complex mixtures of many isomeric forms due in part to the nature of the reactions used to manufacture them. The most preferred compounds are those where R is $C_{12}$ and R' is $C_{12}$ or an alkyl fragment thereof such as $C_1$–$C_8$. In this embodiment, the mixture of (I) contains major fractions wherein X and Y are $NO_2$ and wherein X is $NO_2$ and Y is $SO_3R'$. A particularly preferred blend is one containing different isomers of (III) wherein X is $NO_2$ and the isomeric composition is characterized by variations in the identity of Y and wherein 20–95% of Y is $NO_2$ and 0–20% is H and 0–50% is $SO_3R'$. A still more preferred blend contains different isomers of (III) wherein X is $NO_2$ and the isomeric composition is characterized by variations in the identity of Y and wherein 20–95% of the isomers are Y is $NO_2$ and 10–20% is H and 10–50% is $SO_3R'$.

The preferred blend may also contain components where X is $NO_2$ and Y is H as well as the isomeric forms where X and Y are $NO_2$, n is 1 and 2, m=3 and wherein R' is most preferably a smaller alkyl group than R but also exists as oligomers of nitrated sulfonates, believed to have structures represented by (I) where n=1,2 or 3 or even higher oligimers.

TABLE 1

| ACCEPTABLE ISOMERIC COMPOSITION RANGES OF COMPOUND (I) | | | | |
|---|---|---|---|---|
| X = $NO_2$ Y = Variable n = 0 | (1) | (2) | (3) | (4) |
| Y = H | 0–5 | 0–5 | 0–5 | 15–20 |
| Y = $NO_2$ | 45–55 | 75–80 | 10–20 | 30–50 |
| Y = $SO_3R'$ | 45–55 | 10–20 | 75–80 | 30–50 |

The preferred method of obtaining the isomeric blends of Structure (I) is as a reaction product formed by the process comprising the steps of:

a) reacting an unsubstituted higher alkyl phenol with an excess of sulfuric acid for a time sufficient to allow the exotherm to raise the reaction temperature of the mixture to form a first reaction mixture;

b) adding to the first reaction mixture an excess of nitric acid to form said reaction product in an organic phase suspended in an aqueous phase;

c) separating the organic phase from the aqueous phase; and d) isolating the reaction product in the organic phase.

The preferred reaction product is one using as the starting material a higher alkyl phenol substituted at the para position with $C_9$–$C_{20}$ branched or linear alkyl such as para-dodecylphenol. Commercial forms of dodecylphenol which are available have about 97% para and 3% ortho substitution of the alkyl unit. The alkyl component is believed to be a complex isomeric blend of various branched and straight chain alkyl units of from $C_{12}$ down to $C_9$, although the amount of $C_{11}$ to $C_9$ components is small.

The reactants may be added in either order, either acid to alkyl phenol or alkyl phenol to acid. The temperature for the sulfonation step may range from 25° to 90° C., preferably from 25° to 60° C., most preferably about 50° C. The concentration of sulfuric acid is not critical but is preferably 95% and above. The molar equivalents of sulfuric acid to alkyl phenol may range from 1.5 to 5.0, preferably 2.0 to 4.5, most preferably 2.1 to 4.4.

The second stage nitration step is performed under relatively mild conditions to minimize the dealkylation of the alkyl phenol. The temperature range may vary depending upon the heat transfer efficiency of the vessel. Preferably temperature should be between 45° and 100° C., more preferably 60° to 100° C. and most preferably 80° to 90° C. The molar equivalence of nitric acid is variable, preferably between 1.5 and 4.4, more preferably between 1.9 and 4.0, and most preferably between 2.0 and 2.5.

In one aspect, this invention is directed to a vinyl aromatic polymerization inhibitor system comprising:

the reaction product of a $C_9$–$C_{20}$ alkyl phenol with sulfuric acid and nitric acid; and, optionally, an aryl or alkyl-substituted phenylenediamine compound of formula II

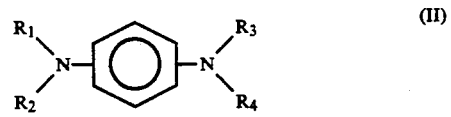

wherein $R^1$ is $C_1$–$C_{12}$ alkyl, $C_6$–$C_{10}$ aryl or $C_7$–$C_{16}$ alkaryl; and $R^2$, $R^3$ and $R^4$ are independently selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl.

In still a further aspect, this invention is directed to a vinyl aromatic composition stabilized against polymerization, said composition comprising a vinyl aromatic compound together with a reaction product of a $C_9$–$C_{20}$ alkyl phenol with sulfuric acid and nitric acid (I), and optionally, a phenylenediamine of formula II. In yet another aspect, this invention is directed to a method for inhibiting the polymerization of vinyl aromatic compounds, which method comprises blending a polymerization inhibiting effective amount of the stabilization system of this invention to the vinyl aromatic to be stabilized.

Particularly suitable reaction product of a $C_9$–$C_{20}$ alkyl phenol with sulfuric acid and nitric acid (I) which can be employed herein are those wherein the alkyl phenol used contains an alkyl group of from 10 to 15 carbon atoms. These alkyl groups can be either branched or straight chains and all reference to "alkyl" in this specification is meant to include such branched or straight chain and optionally cyclic alkyl structures as well. A more preferred alkyl phenol is represented by an alkyl substituent containing 12 carbon atoms. Such a compound is p-dodecylphenol, which is commercially available from Schenectady Chemicals, Inc.

Illustrative of the preferred phenylenediamine compounds of Structure (II) which may be employed include N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine. Moreover, mixtures of phenylenediamine compounds may also be employed. The phenylenediamine compounds may be of the oxygenated species as described in U.S. Pat. No. 4,774,374 to Abruscato et al.

An important advantage of this invention is that the polymerization inhibitors of Compounds (I) do not need air to function. As illustrated by the following examples, the presence of air may add to the efficacy of the inhibitors of the present invention, particularly if component b is present, as stated above. Air or oxygen is not required for the inhibitors of this invention to function. Some manufacturers of vinyl aromatic compounds, such as styrene, prefer to distill said compounds under vacuum, i.e., without air. Thus, the stabilizer compositions of the instant invention provide a much desired advantage to these vinyl aromatic compound manufacturers.

The reaction product of a $C_9$–$C_{20}$ alkyl phenol with sulfuric acid and nitric acid and the phenylenediamine compounds (II) of this inventions are generally employed in weight ratios of between about 10:1 and about 1:10. Preferably, weight ratios of between about 4:1 and about 1:4 are employed, with a ratio of about 1:1 being particularly preferred.

The polymerization inhibitor compositions of this invention may further comprise an aromatic hydrocarbon solvent. Illustrative of such solvents are benzene, toluene, xylene, ethylbenzene and other alkyl-benzenes as well as vinyl aromatic compounds themselves such as styrene, alpha-methylstyrene and the like. Typically, when solvents are employed the hydrogenated precursors of the vinyl aromatic to be stabilized are the preferred solvents. Thus, for the stabilization of styrene, ethyl benzene is the preferred solvent. Similarly for the stabilization of alpha-methylstyrene, isopropylbenzene is the preferred solvent.

Illustrative of the vinyl aromatic compounds which may be stabilized against polymerization by the process of this invention are styrene, alpha-methylstyrene, vinyltoluene and divinylbenzene, as well as halogenated species thereof.

The stabilized vinyl aromatic composition of this invention may be in the form of a reaction mixture additionally comprising the starting materials of the vinyl aromatic compound to be stabilized as well as by-products of the production process. Thus, in the case of styrene, the reaction mixture will typically include starting materials such as benzene, ethyl benzene and ethylene, as well as by-products such as diethylbenzene, vinyltoluene and the like.

The primary use of the polymerization inhibitor systems of this invention is to prevent the polymerization of vinyl aromatics during purification and/or distillation to remove unreacted starting materials and distillable by-products. Typically, this involves the sequential distillation of the vinyl aromatic reaction product through a plurality of distillation columns. In the first of such columns, a relatively large amount of starting material and by-products will be present, while in the last column essentially pure vinyl aromatic compound (plus polymerization inhibitors and heavy, nondistillable byproducts) will be present.

The method of this invention involves adding to a vinyl aromatic compound an effective amount of the inhibitor package. When the polymerization inhibitor system of this invention, using both components (I) and (II) specified above, is employed during the purification and/or distillation of vinyl aromatic compounds, it is preferred that oxygen, whether in the form of air or otherwise, be present. It should be noted that those polymerization inhibitor systems involving only compound (I) do not require oxygen or air to be present. The presence of air is immaterial to the efficacy of component (I) alone.

It is also noted that the polymerization inhibitor system of this invention will be effective for uses other than during distillation, e.g., during the shipment or storage of vinyl aromatic compounds.

The methods of this invention comprise the addition to a vinyl aromatic composition of an effective amount of the instant polymerization inhibitor system. As employed herein, the term "effective amount" refers to that amount of inhibitor which is needed to prevent the formation of more than about 1 weight percent of vinyl aromatic polymer during distillation at temperatures of between about 90° C. and about 150° C. Although the amount of polymerization inhibitor required will vary somewhat (based upon such factors as the particular vinyl aromatic compound stabilized; the particular benzoquinoneimine and phenylenediamine species employed; and the like) such an effective amount may be readily determined by routine experimentation. In general, such an effective amount will be between about 50 and about 1,500 parts per million by weight of vinyl aromatic compound.

The polymerization inhibitor system of this invention will provide stability against vinyl aromatic polymerization at temperatures typically employed for the purification of vinyl aromatic compounds (i.e., from about 90° to about 140° C.) for periods well in excess of those typically employed for such purification. This stability is achieved without the use of undesirably toxic dinitrophenolic compounds which are generally employed in commercial operations today.

SYNTHESIS EXAMPLE 1

Preparation of the Reaction Product of p-dodecylphenol with Sulfuric Acid and Nitric Acid The reaction mixture was prepared in two reaction steps. In the first step, 2.1 equivalents of reagent grade sulfuric acid (98.8%) was added with stirring to 1 equivalent of p-dodecylphenol (Schenectady Chemical, 99.99% assay, 97% para-isomer, 3% ortho-isomer) and the mixture was allowed to exotherm to from 45° to 50° C.

Immediately after this addition, 2.1 equivalents of 35% nitric acid solution was slowly introduced with stirring at a rate which maintained the temperature of the reaction mixture at 80°–90° C.

The reaction was stopped after the addition, and allowed to settle. The lower aqueous layer was removed. The warm organic layer was allowed to sit for an additional 2 to 24 hours. A second portion of the water was then removed. The organic layer was then poured at a temperature of 60°–80° C. into a boiling 10–20% sodium chloride solution and stirred for 5 minutes. The aqueous salt washing was separated and the product dried under reduced pressure leaving a viscous, brown oil.

The viscous brown oil which constituted the reaction product [hereinafter sometimes referred to as Rx Prod(1)] contained the following proportions of isomers of structure (I):

| | | |
|---|---|---|
| $X = NO_2$ and $Y = H$ | 16% | $n = 0$ |
| $X = NO_2$ and $Y = NO_2$ | 28% | $n = 0$ |
| $X = NO_2$ and $Y = SO_3R'^*$ | 42% | $n = 0$ |
| $X = NO_2$ and $Y = NO_2$ | 10% | $m = 3, n = 1,2,3$ |
| side reactions*** | 4% | — |

*R' is a distribution of $C_1$–$C_4$ alkyl substitutents.
***The remainder of the reaction product was found to be composed of 4 percent of side reaction products not of Structure (I).

The identity of the above itemized fragments were determined by gas chromatography, liquid chromatography, mass spectrometry, and acid/base titration.

Induction Time Testing Protocol

To a fifty milliliter flask charged with forty grams of styrene were added the various amounts and types of inhibitors as indicated in Table 2 below.

The flask was fitted with a magnetic stirrer and septum closure with a syringe needle as a vent and heated in an oil bath to 118° C. (plus or minus 2° C.). The flask was purged with approximately 5 cc/min of air or nitrogen passed beneath the liquid surface during the period of the test. During the test period, samples were removed from the flask periodically and tested for degree of polymerization by measuring the changes in refractive index. The induction time is defined as the point at which one (1) weight percent of the styrene had polymerized, was determined in each example and tabulated.

EXAMPLES 2-5/COMPARATIVE EXAMPLES I-K

The data in Table 2, below, displays the Induction Time Testing protocol described above used to evaluate efficacy in an air atmosphere of the inhibitor system of this invention compared to DNPC, an industrial standard. The results for Examples 2-5, which are duplicate runs for equal weight inhibitor blends of Synthesis Example 1, a reaction product of a $C_{12}$ alkyl phenol with sulfuric acid and nitric acid I), and N-(1,4-dimethylpentyl)-N'-phenyl-p-phenylenediamine (PPDA), combined at a 1:1 ratio. All Table 2 runs were made at 100 ppm of inhibitor.

TABLE 2

| Blend or Example | Composition | Atm. | Minutes |
|---|---|---|---|
| 2 | PPDA/Rx Prod(1) | air | 130 |
| 3 | PPDA/Rx Prod(1) | air | 120 |
| 4 | PPDA/Rx Prod(1) | air | 140 |
| 5 | PPDA/Rx Prod(1) | air | 140 |
| I | DNPC | air | 55 |
| J | DNPC | air | 55 |
| K | DNPC | air | 60 |

Notes for Table 2:
PPDA = N-(1,4-dimethylpentyl)-N-phenyl-p-phenylenediamine
RxProd(I) = reaction product of Synthesis Ex. 1
DNPC = Dinitro-p-cresol The data in Table 2 indicates that longer induction times in air for the non-toxic blends of the instant invention are far superior to the induction times for the industry standard, DNPC.

The induction times for Rx Prod(1): PPDA blends are much longer, and in fact serendipitously shown an unexpected degree of polymerization inhibition over those of the comparative examples. The data indicates that in the presence of air, unexpected synergism exists when RxProd(1) and a phenylenediamine of this invention are combined as vinyl aromatic polymerization inhibitors. The induction time evaluation of Table 2 is a screening evaluation. The following continuous distillation protocol simulates the actual conditions in a commercial scale large distillation column where ethylbenzene and styrene are being continuously fractionated to separate the desired styrene monomer from the ethylbenzene solvent/initial reactant. It is in these columns where undesireable polymerization of the vinyl aromatic compounds must be successfully suppressed by the inhibitors system. The following runs show the superiority of the inhibitor system of this invention.

EXAMPLE 6-8/COMPARATIVE EXAMPLES L-N Continuous Distillation Experiments

All distillation testing was performed using a 50 tray 1-inch Oldershaw vacuum jacketed column equipped with an overhead reflux splitter, condenser, and calibrated take-off vessel. The entire distillation unit is attached to a vacuum pump and traps via the top of the condenser.

The column was fitted into a reboiler which consists of a 500 ml round bottom flask equipped with a peristaltic take-off pump and tars collection vessel. The reboiler is heated with a heating mantle.

The feed is introduced via a peristaltic pump through a preheated tube onto the 45th tray. Pressure gauges are placed close to the top and bottom of the apparatus to allow the monitoring of pressure across the column.

To the pot is added 290 ml of styrene containing the inhibitor to be tested at the level to be tested. All styrene used in these experiments is stripped of its shelf inhibitor by flash distillation on a rotary evaporator prior to use.

Added to the 45th tray is a feed stream heated to about 115° C. composed of a 60:40 styrene/ethylbenzene mixture containing the inhibitor to be tested. This feed is added at a rate of about 3.3 mL/minute.

The distillation is run at a reflux ratio of 10:1 and a pot temperature of 118° C. plus or minus 1° C. which is controlled by pressure (about 16 inches Hg). Distillate is taken off from the top at a rate of about 1.7 mL/min and liquid removed from the pot at a rate of about 1.6 mL/min, keeping a constant pot volume and to provide a 2-hour residence time.

Under these conditions, a >99% styrene composition is attained in the pot during the duration of the test, which is 8-12 hours. Equilibrium is attained after 4-6 hours.

A sample is taken from the pot every hour and the polymer level determined by turbidity using a spectrophotometer. In the following table, the standards used to gauge relative performance of the experimental candidates are dintro para-cresol and dinitro sec-butyl phenol, which give polymer levels of about 1%. The polymer levels reported in Table 3 represent the amount of polymer made in the reboiler after the column attains equilibrium, expressed as grams polymer/grams styrene in the feed, converted to percent.

TABLE 3

| Dynamic Distillation Column Testing | | | |
|---|---|---|---|
| Example | Inhibitor | Level (ppm) | Polymer Level |
| 6 | RxProd(1) | 500 | 0.09 |
| 7 | RxProd(1) | 500 | 0.08 |
| 8 | RxProd(1) | 250 | 0.37 |
| L | DNNP(C9) | 500 | 0.6 |
| M | DNBP(C4) | 500 | 1.01 |
| N | DNPC(C1) | 500 | 0.92 |

RxProd(I) = reaction product of Synthesis Ex. 1
DNNP = 2,6-dinitro-4-nonylphenol
DNBP = 2,6-dinitro-4-butylphenol
DNPC = Dinitro-p-cresol As can be seen from the data in Table 3, when tested in a continuous distillation column, RxProd(1) shows unexpectedly high performance over other dinitrophenolics tested; that is, the polymer make is less than 1% when the RxProd(1) is used as an inhibitor. It can also be seen that this candidate shows sensitivity to use level; even at half loading, RxProd(1) outperforms the other dinitrophenolics.

Another benefit of the polymerization inhibitors of the instant invention is that any undesired polymer formed is of lower molecular weight and lower viscosity than the polymer formed when using the inhibitor species currently in use. This undesired polymer, often referred to as tars, is a waste material which presents equipment fouling and disposal problems for styrene manufacturers. The amount of high polymer (species with molecular weight >1000) formed when the inhibitor of Example 1 is used is negligible, as determined by GPC or turbidity analysis of the resulting tars.

The following table is a comparison of the acute oral LD50 values for various common materials. It is noted that the higher the value of LD50, the less toxic the material is. The polymerization inhibitors of this invention, identified as "RxProd(1)" are placed between ethanol and table salt in this determination. The other dinitrophenols have very low values of LD50 indicating much higher toxicity characteristics.

TABLE 4

Comparative Toxicity Data

| COMPOUND | ORAL LD50 (mg/kg) |
| --- | --- |
| Sucrose | 29,700 |
| Ethanol | 7,080 |
| RxProd(1) | 5,616 |
| Sodium Chloride | 3,000 |
| DNNP(C9) | 50 |
| DNPC(C1) | 80 |
| DNBP(C4) | 30 |

The data presented above indicate that the reaction products and blends of the instant invention represent a significant improvement in the attempt to inhibit polymerization of vinyl aromatic species in an environmentally responsible and safe manner. Both the oral and dermal LD50 values for the reaction products of this invention are more favorable than those for the materials used heretofore.

Added to these positive factors in support of the use of RxProd(I) as polymerization inhibitor for vinyl aromatics is the fact that it is a liquid at room temperature. The dinitrophenolics in current use are solids. A liquid material is preferred by the manufacturers due to ease of use and shipping of material. The solubility of RxProd(1) is both styrene and ethylbenzene is >90%; the solubility of DNPC, DNOC, and DNP in ethylbenzene or styrene is less than 25%.

This factor, when coupled with the outstanding performance of the reaction products and blends of this invention as seen in the preceding Tables, is a highly desirable and serendipitous combination.

The above embodiments and examples illustrate the scope and spirit of the instant invention. These embodiments and examples will make apparent to those skilled in the art, other embodiments and examples within the scope of the present invention. Therefore, the instant invention should be limited only by the appended claims.

We claim:

1. A compound represented by structure (I)

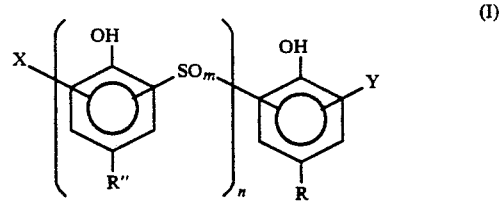

wherein R is $C_9$–$C_{20}$ alkyl, Y is $SO_3R'$, R' is $C_1$–$C_{20}$ alkyl, X is $NO_2$, and R" is H or $C_1$–$C_{20}$ alkyl, m is 2 or 3 and n is 1,2,3.

2. A Compound according to claim 1 wherein X and Y are ortho to the OH.

3. The Compound according to claim 1 wherein R is $C_{12}$.

4. A compound represented by structure I

I:

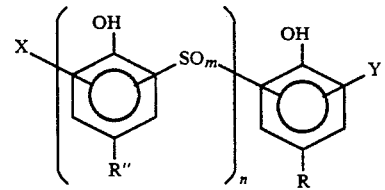

wherein R is $C_9$–$C_{20}$ alkyl, Y is $SO_3R'$, R' is $C_1$–$C_{20}$ alkyl, X is $C_1$–$C_{20}$ alkyl, and R" is H or $C_1$–$C_{20}$ alkyl, m is 2 or 3 and n is 1,2,3.

5. A compound represented by structure I

I:

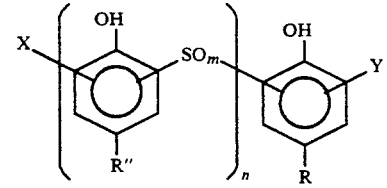

wherein R is $C_9$–$C_{20}$ alkyl, Y is $NO_2$ or H, X is $NO_2$ or $C_1$–$C_{20}$ alkyl, and R" is H or $C_1$–$C_{20}$ alkyl, m is 2 or 3 and n is 1,2,3.

* * * * *